United States Patent [19]

Braatz et al.

[11] Patent Number: 5,169,720

[45] Date of Patent: Dec. 8, 1992

[54] PROTEIN NON-ADSORPTIVE POLYUREA-URETHANE POLYMER COATED DEVICES

[75] Inventors: James A. Braatz, Beltsville; Aaron H. Heifetz, Columbia; Clifton L. Kehr, Silver Spring, all of Md.; Richard A. Wolfe, Ellisville, Mo.

[73] Assignee: W. R. Grace & Co.-Conn., New York, N.Y.

[21] Appl. No.: 665,498

[22] Filed: Mar. 6, 1991

Related U.S. Application Data

[63] Continuation-in-part of Ser. No. 175,880, Mar. 31, 1988, abandoned, which is a continuation-in-part of Ser. No. 932,080, Nov. 18, 1986, abandoned, and a continuation-in-part of Ser. No. 130,826, Dec. 9, 1987, abandoned, and a continuation-in-part of Ser. No. 135,878, Dec. 21, 1987, abandoned.

[51] Int. Cl.$^5$ .............................................. B32B 27/40
[52] U.S. Cl. ................................. 428/423.1; 528/48; 528/52; 528/53; 528/59; 528/904; 427/2; 427/207.1; 427/221; 427/435; 210/500.24; 428/423.9; 428/424.2; 428/424.6; 428/425.1; 428/425.5; 428/425.6; 604/8; 604/19; 604/403
[58] Field of Search ....................... 528/48, 52, 53, 59, 528/904; 427/2, 207.1, 221, 435; 210/500.24; 428/423.1, 424.2, 423.9, 424.6, 425.1, 425.5, 425.6; 604/8, 19, 403

[56] References Cited

U.S. PATENT DOCUMENTS

| | | | |
|---|---|---|---|
| 3,719,050 | 3/1973 | Asao | 405/464 |
| 3,847,722 | 11/1974 | Kistner | 220/81 A |
| 3,903,232 | 9/1975 | Wood et al. | 264/157 |
| 3,939,105 | 2/1976 | Jones, Jr. et al. | 521/63 |
| 3,939,123 | 2/1976 | Matthews et al. | 528/60 |
| 4,048,064 | 9/1977 | Clark, III | 210/23 |
| 4,118,354 | 10/1978 | Harada et al. | 524/711 |
| 4,127,124 | 11/1978 | Claggett et al. | 128/156 |
| 4,137,200 | 1/1979 | Wood et al. | 521/159 |
| 4,237,229 | 12/1980 | Hartdegen et al. | 435/182 |
| 4,241,537 | 12/1980 | Wood | 47/77 |
| 4,381,332 | 4/1983 | Fulmer et al. | 428/288 |
| 4,403,083 | 9/1983 | Marans et al. | 528/44 |
| 4,644,033 | 2/1987 | Gnanou et al. | 529/590 |
| 4,794,090 | 12/1988 | Parham et al. | 436/531 |

FOREIGN PATENT DOCUMENTS

| | | |
|---|---|---|
| 205815 | 12/1986 | European Pat. Off. |
| 333899 | 4/1989 | European Pat. Off. |
| 3239318 | 5/1983 | Fed. Rep. of Germany |
| 2275494 | 1/1976 | France |
| WO83/00695 | 3/1983 | PCT Int'l Appl. |
| WO86/02933 | 5/1986 | PCT Int'l Appl. |
| WO88/00214 | 1/1988 | PCT Int'l Appl. |

OTHER PUBLICATIONS

Coury et al., "Biomedical Uses of Polyurethanes"; *Advances in Urethane Science and Technology*; vol. 9, pp. 130–168 (1984).

Seifert et al., "Evaluation of In Vivo Adsorption of Blood Elements onto Hydrogel-Coated Silicone Rubber by Scanning Electron Microscopy and Fourier Transform Infrared Spectroscopy"; J. Biomed. Matls. Res., vol. 19, pp. 1043–1071 (1985).

Gregonis et al., "Poly(ethylene glycol) Surfaces to Minimize Protein Adsorption".

*Primary Examiner*—John Kight, III
*Assistant Examiner*—S. A. Acquah
*Attorney, Agent, or Firm*—Beverly K. Johnson

[57] ABSTRACT

Polymer-coated medical and laboratory devices are disclosed which are characterized by their biocompatibility and resistance to nonspecific protein adsorption. The polyurea-polyurethane coatings of this invention are prepared from high molecular weight isocyanate end-capped prepolymers substantially or exclusively comprised of ethylene oxide units. At least 75%, preferably at least 90%, of the prepolymer units are oxyethylene-based diols or polyols having molecular weights of about 7000–30,000, with essentially all of the hydroxyl groups capped with polyisocyanate prior to formation of the hydrated polymer coating.

27 Claims, No Drawings

PROTEIN NON-ADSORPTIVE POLYUREA-URETHANE POLYMER COATED DEVICES

This is a continuation-in-part U.S. Ser. No. 175,880, entitled "Protein Non-Adsorptive PolyureaUrethane Polymer Coated Devices", filed Mar. 31, 1988, now abandoned, which is a continuation-in-part of U.S. Ser. No. 932,080, entitled "Biocompatible Polyurethane Hydrated Polymers" (J. A. Braatz and C. L. Kehr), filed Nov. 18, 1986, now abandoned and U.S. Ser. No. 130,826, entitled "Biocompatible Polyurea-urethane Hydrated Polymers" (J. A. Braatz and C. L. Kehr) filed Dec. 9, 1987, now abandoned, and a CIP of U.S. Ser. No. 07/135,878, filed Dec. 21, 1987, now abandoned.

BACKGROUND OF THE INVENTION

This invention relates to synthetic hydrophilic polymers, and to medical and laboratory devices coated therewith. More specifically, this invention relates to a unique series of crosslinked polyurea-urethane polymer coatings formed from high molecular weight isocyanate end-capped prepolymers which are substantially comprised of ethylene oxide units. These hydrophilic polymers are characterized by their biocompatibility and by their unique surface which resists nonspecific protein adsorption. Medical and laboratory devices for which these properties are desired can be coated with the polymers to provide an improved biocompatible and low protein adsorptive surface thereon.

Numerous polyurethane polymers have been previously identified, among them both foamed and nonfoamed materials. Of the nonfoamed materials, quite a few hydrogel polymers, prepared from various prepolymers, have been prepared and used for widely varying applications. Typically, hydrogels are formed by polymerizing a hydrophilic monomer in an aqueous solution under conditions such that the prepolymer becomes crosslinked, forming a three-dimensional polymeric network which gels the solution. Polyurethane hydrogels are formed by polymerization of isocyanate-end capped prepolymers to create urea and urethane linkages.

Representative examples of previously disclosed polyurethane hydrogels include the following: U.S. Pat. No. 4,241,537 (Wood) discloses a plant growth media comprising a hydrophilic polyurethane gel composition prepared from chain-extended polyols; random copolymerization is preferred with up to 50% propylene oxide units so that the prepolymer will be a liquid at room temperature. U.S. Pat. No. 3,939,123 (Matthews) discloses lightly crosslinked polyurethane polymers of isocyanate terminated prepolymers comprised of poly(ethyleneoxy) glycols with up to 35% of a poly(propyleneoxy) glycol or a poly(butyleneoxy) glycol. In producing the Matthews prepolymer, it is taught that the ratio of isocyanato groups to hydroxyl is from about 1.2 to 1.6 equivalents of isocyanato per equivalent of hydroxyl. A solids content of 25 to 40 wt. % is employed in forming the hydrogel. U.S. Pat. No. 4,118,354 (Harada) discloses a polyurethane hydrogel prepared from the reaction product of a polyisocyanate with a polyether which comprises a plurality of alkylene oxides, 50 to 90% by weight of which is ethylene oxide, added at random to a polyalcohol having at least two terminal hydroxyl groups. Harada requires that the prepolymers be liquid or pasty at room temperature in order to avoid having to liquify the prepolymer either by heating it or diluting it with a solvent. U.S. Pat. No. 4,381,332 (Fulmer et al.) discloses a polyurethane gel adhesive to form a nonwoven fabric, prepared from a prepolymer having molecular weight of at least 3000, made from an aliphatic polyisocyanate capped polyether polyol; up to 50% may be butylene oxide and propylene oxide. U.S. Pat. No. 3,719,050 (Asao) teaches a soil stabilization method in which a polyurethane prepolymer having terminal isocyanate groups is injected into the ground; the prepolymer may be diluted with water or may be reacted with water present in or flowing through the soil.

It can be seen that numerous combinations of molecular weights and prepolymer composition have been patented. Typically, prior hydrogel systems have required that the polyols and prepolymers be liquid or pasty at room temperatures to avoid having to melt the composition. This requirement places restraints on the composition of the polyols and prepolymers. As a rule, the prior art teaches copolymerization of propylene oxide or butylene oxide units sufficient to yield liquid polyols and prepolymers. However, inclusion of these monomer units also serves to decrease the hydrophilicity of the prepolymer. Additionally, low molecular weight prepolymers have been used to achieve this end.

In addition, biocompatibility is an increasingly desirable characteristic for polymeric coatings, which would find numerous uses in the health care field if the appropriate properties can be obtained. However, many conventional hydrogels are not taught to be biocompatible.

Finally, prior art polymers tend to adsorb proteins from solutions with which they are brought into contact. This is a particular problem in attempting to utilize conventional polymers for laboratory and health care applications where proteins are omnipresent. The result may be occlusion or clogging of the polymer, clouding, contamination, assay interference, irritation to adjacent body tissues, or loss of tissue or bodily fluid protein by irreversible adsorption or denaturation. When such polymers are used in contact with the bloodstream, thrombogenesis, complement activation or calcium deposition may result.

SUMMARY OF THE INVENTION

The polyurea-urethane polymer system of this invention provides polymer coatings with highly desirable properties which make them particularly well suited for use in the growing field of biomedical applications for polymers. The polymers of this invention are prepared from a low water content organic solvent solution of a high molecular weight isocyanate end-capped prepolymer substantially or exclusively comprised of ethylene oxide units. At least one surface of a medical or laboratory device is coated with the prepolymer solution, which is crosslinked in place with water. The resulting polymers take the form of a dense or thin coating or impregnant on a substrate, including, under dilute conditions, a monomolecular or substantially monomolecular layer. The coatings and impregnates of this invention are considered gels or hydrogels and are included by those terms unless otherwise noted. The terms gel or hydrogel are meant to refer to polymers which are non-foamed in structure.

It is one of the primary objects of this invention to provide a class of hydrated polymers for which ease of preparation and handling is combined with desirable properties permitting a wide range of end uses. In this regard, the novel prepolymers disclosed herein can be handled and stored in liquid form at ambient temperatures even though these relatively high molecular weight prepolymers, which comprise a very high proportion of ethylene oxide units, and the polyols from which they are prepared, are often solid at ambient temperatures. This significantly facilitates formation of the hydrated polymer coating, as well as enhances the uniformity of the polymer.

It is a further object to provide polymeric surfaces which are hydrophilic and yet display marked resistance to the nonspecific adsorption of proteins.

It is a related object of the invention to provide a class of polyurea-urethane prepolymers and related hydrated polymer coatings which are hydrophilic, transparent and biocompatible.

DETAILED DESCRIPTION OF THE INVENTION

A new class of hydrophilic polyurea-urethane prepolymers and related crosslinked hydrated polymer gels has been found which are uniquely characterized by biocompatibility and resistance to nonspecific protein adsorption and which can be coated onto medical and laboratory devices for purposes of conferring those characteristics on the devices. The hydrated polymers are formed from polymeric monomer units (the prepolymer units) at least 75% of which are oxyethylene-based diols or polyols having molecular weights of about 7000 to about 30,000, with essentially all of the hydroxyl groups of these diols or polyols capped with polyisocyanate. The prepolymers useful in this invention are prepared by reacting the selected diols or polyols with polyisocyanate at an isocyanate-to-hydroxyl ratio of about 1.8 to about 2.2 so that essentially all of the hydroxyl groups of the polyols are capped with polyisocyanate. The prepolymer is coated onto the desired substrate, i.e., onto at least one surface of the device. Polymerization of the prepolymer (the isocyanate-capped diol or polyol) in water or an aqueous solution acts to gel and crosslink the deposited layer of the composition.

The diols and polyols used in this invention predominantly or exclusively are polyoxyalkylene diols or polyols made up of ethylene oxide monomer units. At least 75% of the units should be ethylene oxide, preferably at least 90%, and more preferably at least 95%. Most preferably, substantially all or all of the units should be ethylene oxide. Conventional urethane polymer hydrogel systems typically require inclusion of substantial proportions of propylene oxide or butylene oxide units in the polyols and derivative prepolymers to ensure that they will be liquid or pasty at room temperature. Alternatively, solid or crystalline polyols and derivative prepolymers must be heated to their melting point in order to be handled for use in conventional systems. These requirements are avoided by the present invention. Even 100% ethylene oxide diols or polyols and the derivative prepolymers may be accommodated. Extremely high ethylene oxide content (i.e., greater than 90 or 95%) is in fact preferred, with 100% ethylene oxide-based diols or polyols and derivative prepolymers being the most preferred for this invention.

High molecular weight ethylene oxide-based diols and polyols are used to prepare the prepolymers and hydrated polymers of the present invention. The diol or polyol molecular weight prior to capping with polyisocyanate should be at least about 7000 to 8000 MW, preferably about 10,000 to about 30,000 MW. It is preferred to use trihydroxy compounds (triols) in the preparation of the polyols which are the precursors to the prepolymers and hydrated polymers of this invention. For example, glycerol is a preferred triol. Trimethylolpropane (TMOP), trimethylolethane and triethanolamine are other suitable triols. In addition, tetrols, such as pentaerythritol, may be used to prepare polyols for use in this invention. Triol- or tetrol-based polyols are capped with difunctional or polyfunctional isocyanate compounds as described below to form the prepolymer.

Alternatively, diols of appropriate molecular weight may be used as precursors to the prepolymers of this invention. Diols of appropriate molecular weight are capped with polyfunctional isocyanates as described below to form the prepolymers. High molecular weight polyethylene glycols are particularly useful. Especially desirable in this embodiment are polyethylene glycols of the formula $H(OCH_2CH_2)_xH$ where x is an average number such that the glycol has an average molecular weight of at least about 7000, preferably about 10,000 to about 30,000. Alternatively, diols may be capped with diisocyanates and used in conjunction with crosslinking compounds to form the hydrated polymers described herein. Crosslinking compounds useful for this purpose include polyfunctional amines and polyfunctional isocyanates. In still another alternative embodiment, diols may be mixed with polyols and the resulting mixture reacted with isocyanates to produce the prepolymer of this invention.

The prepolymers of this invention are formed by reacting the hydroxyl groups of the diols or polyols described above with polyisocyanates. "Polyisocyanate" as used herein is intended to refer to both diisocyanates and polyisocyanates, as appropriate, except as indicated by specifying the use of difunctional or polyfunctional isocyanates. Isocyanate end-capped (i.e., isocyanate-terminated) prepolymers are formed. The choice of the polyisocyanate will depend on such factors as selection of the precursor to the prepolymer (i.e., polyol or diol), the degree of handling or shaping required in preparing the polymer, and the anticipated end use of the hydrated, crosslinked polymeric structure.

The selected precursor to the prepolymer influences the choice of polyisocyanate in that the prepolymer structure must lend itself to sufficient crosslinking to gel an aqueous prepolymer solution or to form a crosslinked polymeric coating. In the embodiment in which the precursors to the prepolymers are polyols (that is, triol-based or tetrol-based), difunctional isocyanates are preferred. If desired, polyfunctional isocyanate compounds may also be used with polyols. Mixtures of suitable isocyanates also may be considered.

Where diols are used as the precursors to the prepolymers, they may be reacted with polyfunctional isocyanate compounds to form the prepolymers of this invention. This combination yields prepolymers having sufficient functional groups for crosslinking in the formation of the hydrated polymer. In an alternative embodiment using diols as the precursors to the prepolymers, the diols may be capped with a difunctional isocyanate. In order to achieve sufficient crosslinking in the hydrated polymer prepared from these difunctional prepolymers, they are used in conjunction with a crosslinking compound. The preferred crosslinker is trimethylolpropane ("TMOP"), although others may be used, for example, glycerol, trimethylolethane, pentaerythritol, triethanolamine, polyfunctional amines, polyfunctional isocyanates, and the like.

Aromatic, aliphatic or cycloaliphatic polyisocyanates may be used in any of the above-described embodiments. The use of aliphatic polyisocyanates permits a greater degree of handling and/or shaping since aliphatic isocyanate-capped prepolymers typically require about 20 to 90 minutes to gel to a hydrated polymer state. By contrast, prepolymers capped with aromatic polyisocyanates will gel more rapidly, in about 30 to 60 seconds. In addition, aliphatic polyisocyanates will be preferred when the hydrated polymer is intended to be used in medical applications, because of decreased toxicological considerations. However, hydrated polymers made using aromatic polyisocyanates in the prepolymer are also useful, as well as being suitable for most industrial uses.

Examples of suitable di- and polyfunctional isocyanates are found in the following list:
toluene-2,4-diisocyanate
toluene-2,6-diisocyanate
commercial mixtures of toluene-2,4 and 2,6-diisocyanates
isophorone diisocyanate
ethylene diisocyanate
ethylidene diisocyanate
propylene-1,2-diisocyanate
cyclohexylene-1,2-diisocyanate
cyclohexylene-1,4-diisocyanate
m-phenylene diisocyanate
3,3'-diphenyl-4,4'-biphenylene diisocyanate
4,4'-biphenylene diisocyanate
4,4'-diphenylmethane diisocyanate
3,3'-dichloro-4,4'-biphenylene diisocyanate
1,6-hexamethylene diisocyanate
1,4-tetramethylene diisocyanate
1,10-decamethylene diisocyanate
cumene-2,4-diisocyanate
1,5-napthalene diisocyanate
methylene dicyclohexyl diisocyanate
1,4-cyclohexylene diisocyanate
p-tetramethyl xylylene diisocyanate
p-phenylene diisocyanate
4-methoxy-1,3-phenylene diisocyanate
4-chloro-1,3-phenylene diisocyanate
4-bromo-1,3-phenylene diisocyanate
4-ethoxy-1,3-phenylene diisocyante
2,4-dimethyl-1,3-phenylene diisocyante
5,6-dimethyl-1,3-phenylene diisocyanate
2,4-diisocyanatodiphenylether
4,4'-diisocyanatodiphenylether
benzidine diisocyanate
4,6-dimethyl-1,3-phenylene diisocyanate
9,10-anthracene diisocyanate
4,4'-diisocyanatodibenzyl
3,3'-dimethyl-4,4'-diisocyanatodiphenylmethane
2,6-dimethyl-4,4'-diisocyanatodiphenyl
2,4-diisocyanatostilbene
3,3'-dimethoxy-4,4'-diisocyanatodiphenyl
1,4-anthracenediisocyanate
2,5-fluorenediisocyanate
1,8-naphthalene diisocyanate
2,6-diisocyanatobenzfuran
2,4,6-toluene triisocyanate
p,p',p"-triphenylmethane triisocyanate
trifunctional trimer (isocyanurate) of isophorone diisocyanate
trifunctional biuret of hexamethylene diisocyanate
trifunctional trimer (isocyanurate) of hexamethylene diisocyanate
polymeric 4,4'-diphenylmethane diisocyanate Capping of the selected diols or polyols with polyisocyanates to form the prepolymers of this invention is effected using stoichiometric amounts of reactants. The isocyanate-to-hydroxyl group ratio preferably should be between about 1.8 and about 2.2. Higher ratios may be used but are not preferred since they may lead to problems associated with excessive monomer present in the final products. The capping reaction may be by any convenient method or procedure. For example, the reaction may be carried out at about 20° to about 150° C., under dry nitrogen, for about 2 hours to about 14 days, preferably in the absence of a catalyst. The preferred temperature is about 60° to 70° C. The reaction is terminated when the isocyanate concentration approaches theoretical values. The time period will be a function of the polyisocyanate used and the temperature at which the reaction is conducted. Polymerization occurs much more rapidly when aromatic polyisocyanates are used than with aliphatic polyisocyanates. Similarly, the reaction will be more rapid with increased temperatures.

It is preferred to avoid using an excess of polyisocyanate in preparing the prepolymer. Preferably, an isocyanate-to-hydroxyl group ratio of 2:1 (for example, one diisocyanate molecule per hydroxyl group of the polyol) is used to ensure complete end-capping of the polyol. Complete end-capping eliminates excessively high viscosity in the prepolymer by avoiding undue amounts of chain extension. However, a slight excess of isocyante, i.e., up to about ten percent, can be used.

It is characteristic of the present polymer system that the isocyanate content is very low. This is achieved by employing high molecular weight polyols and by avoiding excessive quantities of isocyanate in the end-capping reaction so that free isocyanate monomers are present at low levels. The isocyanate concentration in the prepolymer should be about 0.1 to about 0.43 milliequivalents per gram, for prepolymers formed from diols or polyols of about 7,000 to 30,000 MW.

Notwithstanding a preference for low isocyanate content, the polymer system described herein affords a greater degree of flexibility in this regard than conventional systems. The presence of an organic solvent in preparing and handling the prepolymer protects against excessive viscosity resulting from the use of insufficient quantities of isocyanate for complete end-capping of the diol or polyol. That is, it permits the use of less than stoichiometric (2:1) quantities of the isocyanate monomer. Chain extension resulting from incomplete end-capping typically results in increased viscosity which may make handling of the prepolymer difficult or impossible. By contrast, the system of this invention tends not to be affected negatively by increased viscosity due to chain extension, or from any other cause, because the solvent serves to maintain the viscosity within a range suitable for convenient handling of the prepolymer.

The organic solvent used in preparing the prepolymer must be compatible with the reactants and with the end use desired for the hydrated polymer. Primarily, the solvent must be one in which the diol or polyol and/or prepolymer can be readily dissolved, preferably at ambient temperatures. Suitable solvents for preparing the prepolymer include acetonitrile, dimethyl formamide, dimethyl sulfoxide, tetrahydrofuran, dioxane, dichloromethane, acetone and methyl ethyl ketone, or mixtures thereof. The solvent must also be compatible with the surface on which the prepolymer coating is to be applied and selection of the solvent will be made with this in mind. Acetonitrile frequently will be preferred. In addition, low water content organic solvents (that is, solvents containing less than about 0.01% water) should be used in preparing the prepolymer.

In one embodiment using an organic solvent, the diol or polyol itself is dissolved in the solvent and is reacted with polyisocyanate while in solution to yield the isocyanate end-capped prepolymer. This embodiment is particularly preferred where the diol or polyol is solid or crystalline at ambient temperatures, that is, for diols or polyols substantially or exclusively comprised of ethylene oxide units and for high molecular weight diols or polyols. In this manner, even crystalline diols or polyols can easily be handled without heating to their respective melting points. Even though the prepolymer formation reaction is conducted at elevated temperatures, utilizing an organic solvent to first place the diol or polyol in liquid form assures good reaction and prepolymer formation.

In another embodiment using an organic solvent, the isocyanate end-capped prepolymer first is prepared and then is dissolved in an organic solvent. This embodiment will be useful where the diol or polyol already is liquid or pasty at ambient temperatures and does not require dissolution in order to prepare the prepolymer. For example, diols or polyols of lower molecular weight or higher propylene oxide or butylene oxide content may be treated in this manner. Use of a solvent at the prepolymer stage is advantageous where increased viscosity occurs due to chain extension of incompletely end-capped diols or polyols.

In addition, organic solvents are used in preparing the hydrated polymer of this invention. During polymerization, the presence of a solvent enables the system to tolerate higher levels of excess isocyanate (over stoichiometric amounts) without causing disruption of the hydrated polymer formation. Carbon dioxide formed by the reaction of excess isocyanate monomer and water simply effervesces due to the system's low viscosity, rather than becoming entrapped to elicit foam formation. In addition, the presence of a compatible organic solvent facilitates the coating of the prepolymer onto the substrate or device surface.

The solvents listed above as being suitable for use in preparing the prepolymer may also be used here. In addition, methanol, ethanol, 2-propanol, methylene chloride and dichloromethane, or mixtures thereof, may be used. However, if methanol is selected, it must be removed promptly (i.e., within a few minutes to several hours) in order to avoid excessive end capping of the isocyanate groups, which will prevent polymerization. The use of "low water content" solvents as described above is not required at this stage and varying amounts of water may be present in the solvent.

The organic solvent used in the preparation of the prepolymer or hydrated polymer most frequently will be removed prior to use of the polymer. The solvent may be removed from the prepolymer prior to curing or may be allowed to evaporate during the process of depositing or coating the prepolymer onto a desired coatable substrate. Alternatively, where a thin polymeric coating is desired, the prepolymer may be adsorbed onto a substrate directly from the solvent solution after which the entire coated substrate may be removed from the solvent. In most cases, the solvent is removed from the hydrated polymer after curing, either by evaporation or by washing with water. In the latter cases, it is necessary to use a solvent which is water soluble. Alternatively, the solvent used to coat the prepolymer onto the substrate may be washed out and replaced with a more chemically compatible solvent or a solvent/water combination.

It may be desired to add an antioxidation agent at some point prior to polymerization, preferably prior to preparation of the prepolymer. Antioxidants are not required to make or use the prepolymers or hydrated polymers of this invention. However, storage and handling properties may be enhanced by such an addition by preventing oxidative breakdown of the polymer or its precursors. Suitable antioxidants include the hindered phenolic compounds. Specific examples are Irganox (TM) (Ciba-Geigy Corp.) and Santonox (TM) (Monsanto Chemical Co.) antioxidants. The antioxidant may be added in amounts of about 0.01 to about 1.0%, preferably about 0.02 to about 0.1%, based on the weight of the polyol or precursor to the prepolymer.

Gelling or curing is accomplished by the addition of a stoichiometric excess of water or aqueous solution, relative to the total available isocyanate groups. Preferably, water alone is used, but solutes or particulates may be present, if desired. Solutes which react with the isocyanate groups will become an integral part of the hydrogel. Care should be taken with such solutes since too high a concentration may result in excessive end-capping of the prepolymer to such an extent that polymerization will be precluded.

Polymerization begins to occur spontaneously with formation of urea upon contact of the isocyanate groups of the prepolymer with the water. Catalysts or crosslinking agents other than water are not required but are considered optional. Catalysts may be used if means are taken to avoid toxicological problems with the end products (i.e., soaking in water or buffer to remove the catalyst) where the end product will be used in contact or conjunction with patients. Suitable catalysts include organic tin salts (e.g., dibutyltin dilaurate) and tertiary amines. Suitable crosslinking agents include primary and secondary polyamines and polyfunctional isocyanates. As used herein, "polyhydric" shall also include "dihydric" and "polyfunctional" shall also include "difunctional". Crosslinking agents preferably are employed in stoichiometric or near stoichiometric amounts, although the exact proportions are not critical.

As polymerization begins to occur, gelling takes place. Prior to gelling, the prepolymer solution may be shaped, poured or handled as necessary. At the gelling stage, the hydrated polymer takes on the physical form of the final cured product, forming a semisolid elastic matrix, although unreacted isocyanate groups still will be present. Gelling time may be on the order of from about thirty seconds to about one hour. Upon gelation, the mixture loses its ability to flow, becoming a jelly-like solid or semi-solid mass. The polymer continues curing until the chemical reaction of all residual isocyanate groups is complete or approaches completion. Complete reaction may take hours, days or weeks, depending on the conditions and the polyisocyanate used. The curing time may be shortened by addition of chain terminating or inactivation agents, such as ethanolamine, which cause end-capping without chain extension. The final polymer product is a polyurea-urethane.

To set the hydrated polymer, only gelation is required. However, complete or substantially complete curing is necessary in order to produce a hydrated polymer which completely resists nonspecific protein binding. Complete isocyanate reaction may be ensured by soaking the polymer in water to reduce or eliminate the availability of residual isocyanate groups, or by incorporating chain terminating agents as described above. This eliminates residual isocyanate groups which may bind proteins which come into contact with the hydrated polymer.

Gelling and curing time will vary, depending in part on the concentration of prepolymer present in the solution from which the hydrated polymer is formed. Gelling time decreases with higher prepolymer concentrations. In addition, gelling time depends on the type of polyisocyanate used in preparing the prepolymer. Aromatic polyisocyanate end-capped prepolymers will gel rapidly, usually reacting in somewhat less than one minute, although the curing time may be longer. Prepolymers capped with aliphatic polyisocyanates have a longer gelling time, typically about 20 to 90 minutes, and may take from up to several hours to several weeks for complete curing. Curing time will be influenced by conditions of temperature, humidity, and the like. Thinner coatings can be expected to cure more quickly than thicker coatings.

When the polymers of this invention are prepared as a coating in the form of a thin film or a monomolecular or substantially monomolecular layer, a distinction between gelling and curing is not readily apparent. The prepolymer-organic solvent solution is deposited on a substrate and excess organic solvent is removed. Atmospheric moisture may be sufficient for polymerization of the gel coating or layer. Alternatively, water may be added to the coated substrate (i.e., via a water spray or a water bath) to promote chain extension and crosslinking of the polymer on the substrate surface. This crosslinking is necessary to stabilize the coating, which otherwise would wash off under certain conditions, such as high water flow rates, or high or low pH, for example. The coating is subjected to this water treatment for about 15 minutes to about 24 hours, or longer, to ensure complete or substantially complete reaction of the isocyanate groups. If desired, the coating may be treated with a chain terminating agent, such as ethanolamine, to ensure reaction of the residual isocyanate groups.

According to the method of this invention, the isocyanate-capped prepolymer is placed in solution in an organic solvent, preferably acetonitrile. The prepolymer concentration in the solution can be varied as desired, preferably between about 0.01% and about 10.0% by weight, most preferably between about 0.1% and about 5%. Varying the concentration will affect the thickness of the coating, with higher prepolymer concentrations yielding thicker coatings. Therefore, it may be desired to adjust the concentration depending on the coating thickness needed, the area and type of substrate to be coated, etc.

The prepolymer solution is placed in contact with the substrate to be coated, for sufficient time to allow the prepolymer to become deposited on, adsorbed to or impregnated in the substrate surface. Typically, about one to two hours at room temperature will be adequate, although certain substrates may require a longer contact time for a suitable coating to form. Excess solution is then drained or otherwise removed from the coated substrate. Substrates such as silica lend themselves to coating in this fashion. The coating typically will be thinner than coatings formed by deposition as described below.

For other substrates, the organic solvent-prepolymer solution is coated or deposited onto the substrate in the quantity desired. The coated substrate is then dried to produce the polymer-coated surface. By thorough drying, the polymer is forced against the substrate surface. Drying may be by air drying, vacuum drying, heat or any other means which will not unduly disturb the deposited coating.

The coated surface is contacted with water to crosslink the polymer in place on the substrate. This preferably is by immersion in a water bath, although other means, such as spraying or misting, may be employed. Ambient temperatures are preferred, but temperatures of about 15° to about 100° C. may be used if desired. Atmospheric moisture itself may be sufficient. Contact with water preferably should be for a sufficient period to completely polymerize the coating, as described above. An aqueous solution of crosslinking agents (for example, a solution of Tris-(hydroxymethyl aminomethane), may be substituted for the water. The coated substrate is then dried and is ready for use.

The surface properties of the hydrated polymer coating described herein are unique and offer significant advantages over conventional polymer coatings. In particular, the coatings of this description are resistant to nonspecific protein adsorption. This feature avoids problems associated with undesirable protein adsorption, such as cloud formation, occlusion, etc. As a result, the hydrated polymer products and derivatives of this invention will have longer useful lives in applications where contact with proteins is likely. Moreover, the polymers of this invention are particularly useful for applications in which conventional polymers and hydrogels are unacceptable or undesirable because of protein adsorption or loss of transparency resulting therefrom.

The biocompatibility of the polymers of this invention is related, at least in part, to the polymers' ability to resist protein adsorption. While not limiting the effectiveness of this invention to any specific theory, the unique qualities of these polymers are believed to relate to the use of predominantly or exclusively ethylene oxide-based diols or polyols in the formulation of the prepolymers and hydrated polymers. When the polymers of this invention are used in contact with an aqueous system, the ethylene oxide segments of the polymer attract and complex with water molecules. Consequently, the surface presented to living cells or tissues is predominantly a layer of water. This protective curtain of water renders the underlying synthetic polymeric material noninteractive with proteins. The result is a hydrated polymer which is physiologically acceptable, and which does not remove or denature proteins from the environment in which the polymer is used.

Biocompatibility, as used herein to describe the hydrated polymers of this invention, refers to the resistance to adsorption of protein and to the lack of interactiveness with physiological surfaces, as discussed above. In addition, the hydrated polymers of this invention have been demonstrated to be nontoxic to mammalian cells. Use of aliphatic polyisocyanates in preparation of the prepolymers may further enhance the biocompatibility of the hydrated polymer coating since the potential degradation products of aliphatic polyisocyanates are reported to be significantly less carcinogenic than those of aromatic isocyanates. However, if aromatic polyisocyanates are used, careful washing or other means for removing any unreacted isocyanate and related amine-containing by-products generally will be sufficient to render the hydrated polymer biocompatible.

The finished hydrated polymer is water swellable and is capable of swelling to an extent that it may comprise up to about 95 to 99% water. The volumetric expansion may be tenfold for polymers made with about a 1:5 prepolymer-to-water ratio. Decreasing the relative proportion of prepolymer will allow for increased volumetric expansion. Hydrated polymers made from solutions containing high concentrations of prepolymer versus water tend to form tighter polymeric compositions. Such coatings tend to be less susceptible to expansion, unless a very thin coating is prepared.

The hydrated polymer coatings of this invention are covalently extended and crosslinked and therefore are not readily soluble or degradable in aqueous systems under physiological conditions, which further increases the polymers' suitability for use with living cells or tissues. The physical integrity of the hydrated polymer is maintained when used in an aqueous system, eliminating problems with toxicity and contamination. Moreover, these characteristics make it possible to use the hydrated polymers of this invention in aqueous systems over extended periods with minimal loss of polymer strength or integrity.

The polymer coatings of this invention may be applied to a wide variety of laboratory and medical care instruments and devices. The coatings themselves are transparent and will not interfere visually with any purpose of the coated substrate. If desired, colorants or other compounds may be added. Moreover, the transparent coatings of this invention will remain transparent and unclouded even after steam sterilization or prolonged exposure to a protein-containing environment. Tubing of various types may be coated to increase surface biocompatibility and/or decrease nonspecific binding of proteins. For example, tetrafluoroethylene fluorocarbon polymers (e.g., Teflon (TM) polymer (E. I. duPont de Nemours & Company)), silicone, polyurethane polymers, vinyl polymers (e.g., Tygon (TM) vinyl polymers (U.S. Stoneware Co.)), rubber or other tubing may be coated according to this invention, either inside or outside, or both.

The coated tubing of this invention is ideally suited for use in medical devices or procedures requiring contact with blood or other protein-containing fluids, or requiring contact with tissues. Such applications may be found in externally used artificial organs or extracorpeal therapeutic devices such as, for example, kidney dialysis and hemoperfusion devices as well as implantable or partially implantable artificial organs or devices such as vascular access devices, insulin pump tubing, urinary or venous catheters, etc. In addition, other portions of artificial organ devices may be coated. In an implantable device, for example, the entire external surface area may be coated to increase the device's biocompatibility. All internal blood-contacting portions of a device may be coated to reduce protein binding, thereby reducing or eliminating thrombogenicity.

Other medical devices may be coated, as may various types of labware which is used in conjunction with tissue or cell cultures, protein-containing fluids such as blood or serum, or the like. This would include, but not be limited to, assay plates, supports or membranes, glassware, cell culture or bioreactor devices or assemblies, tubing for blood transfer, blood cell storage bags, filters, pharmaceutical manufacturing and packaging, protein isolation, preparation and purification devices or systems, etc. Any device or apparatus made of glass, polystyrene, silicone, Teflon (TM) polymer (E. I. duPont de Nemours & Company), Tygon (TM) polymer (U.S. Stoneware Co.), polyvinylchloride, polymethylpentene, rubber, metal, wood, and the like may be coated according to this invention. In addition, woven or non-woven cloth or cloth-like materials used in laboratory or medical settings may be coated or impregnated with the polymers of this invention to increase resistance to protein binding, thereby reducing staining from protein sources. Coated articles prepared according to this invention will be particularly useful for reusable systems, devices, etc., in order to minimize cross-contamination and to facilitate protein removal by washing.

Protein quantitation, isolation and purification devices, e.g. assay plates, support or membranes and the like may be coated by the polymers of the invention. Such devices may be in the form of a microporous or nonwoven membrane, particulate porous or nonporous media, or a nonporous device such as a microtiter plate. Microporous materials such as those now utilized for diagnostics will be suitable. Nylon membranes are frequently used. Alternatively, membranes of polypropylene, various polyesters, polyvinyl fluoride, Teflon (TM. E. I. duPont de Nemours & Co.) or cellulose may be used. Membranes of woven or nonwoven materials may be of suitable surface area such that the test fluid and any solutes contained therein will wet the surface and may or may not pass through the support. Membranes with pore sizes of about 0.05 or less to about 5.0 microns or greater are typically used. The membrane material must be insoluble in the solvents used both in preparing the support or membranes.

Alternatively, porous or nonporous particulate supports may be used. For example, silica gel, charcoal and other inorganic or organic particle supports would be suitable. The particle size will be chosen according to the format in which the support will be used. For example, if the matrix will be in a column or packed bed configuration, the particles must be of sufficient size to allow flow of the test fluid and reagent solutions through the bed. One micron beads may be desirable for use in this embodiment. Again, the material chosen must be insoluble in the solvents used in preparing the matrix and conducting the assay.

In another alternative embodiment, the support matrix may be a nonporous assay device, such as a microtiter plate. Devices such as this typically are composed of materials such as polystyrene, polypropylene, polyvinylchloride and the like. Care should be taken in preparing support of this embodiment either to select solvents which will not compromise the integrity of the support, or to quickly remove the solvent after the coating step before the support can be eroded or otherwise damaged.

The coated supports may be used in various medical and laboratory procedures in which contact with blood or other protein-containing fluids is likely. For example, coated silica and charcoal particles may be used as a media for protein removal in a hemoperfusion system where it is desirable to remove toxic contaminants or pharmacuetical agents from blood. Coated silica and charcoal particles are also suitable for use in size exclusion chromatography of protein based on the molecular size of the protein. The nature of the polymer coating of the invention allows chromatography on the polymer-coated silica or charcoal particles without protein-silica or protein-charcoal interaction.

Coated plates and membranes may be used in diagnostic and analytical testing to minimize the adsorption of protein on contact with contaminated test fluids. The polymer coatings of the invention increase the reliability of the diagnostic assays by significantly reducing susceptibility to false results and to blinding results due to nonspecific protein adsorption on the assay support or membrane.

The examples which follow are given for illustrative purposes and are not meant to limit the invention described herein. The following abbreviations have been used throughout in describing the invention.
A—Angstrom(s)
BSA—bovine serum albumin
° C.—degrees Centigrade
cm—centimeter(s)
DMEM—Dulbecco's Modified Eagle's Medium
DI—deionized
ELISA—enzyme-linked immunosorbent assay
F12—F12 cell culture medium
gm—gram(s)
Hg—mercury
i.d.—inner diameter
IDPI—isophorone diisocyanate
IgG—Immunoglobulin G
IU—International unit(s)
l—liter
M—molar
$m^2$—square meter(s)
meq—milliequivalent(s)
mg—milligram(s)
min—minute(s)
ml—milliliter(s)
mm—millimeter(s)
μm—micrometer
MW—molecular weight
ngm—nanogram(s)
PBS—phosphate buffered saline
%—percent
Tm—trademark
UV—ultraviolet
v—volume
wt—weight

EXAMPLE I

Preparation of Prepolymer A

The polyol used to prepare the prepolymers of this invention, Pluracol V7 (TM) (BASF), a 7000 MW triol copolymer of ethylene oxide (75%) and propylene oxide (25%), was deionized and dried. Following this deionization procedure, 1687.46 gm Pluracol V7 was mixed with 165.0 gm isophorone diisocyanate (IDPI) and 0.93 gm Santonox R (TM) (Monsanto Chemical Co.) and heated at 70° C. under dry nitrogen. Isocyanate levels were determined by addition of dibutylamine and back titration with standard acid. Fourteen days were required for the isocyanate concentration to reach 0.47 meq/gm (0.39 meq/gm = theoretical). The resulting prepolymer, designated Prepolymer A, was liquid at room temperature.

EXAMPLE II

Preparation of Prepolymer B

A prepolymer was formed by mixing 300.0 gm deionized and dried TPEG10000 (TM) (Union Carbide Corp.) with 22.0 gm IPDI and 0.16 gm Santonox R. TPEG10000 is a 10,000 MW triol prepared from 100% homopolymeric ethylene oxide. The mixture was heated at 70° C. under dry nitrogen as in Example I, until isocyanate values reached 0.36 meq/gm (theoretical =0.28 meq/gm). This prepolymer, designated Prepolymer B, formed a solid when cooled to room temperature.

EXAMPLE III

Preparation of Prepolymer C

A prepolymer was formed by mixing 403.0 gm deionized and dried TPEG20000 (TM) (Union Carbide Corp.) with 14.78 gm IPDI and 0.21 gm Santonox R. TPEG20000 is a 20,000 MW triol prepared from 100% homopolymeric ethylene oxide. To this mixture 515.0 ml acetonitrile was added to prevent solidification. The resulting mixture was heated as in Example I for eleven days until an isocyanate content of 0.147 meq/gm, corrected for solvent (theoretical =0.145 meq/gm), was reached. The prepolymer, designated Prepolymer C, was a liquid at room temperature.

EXAMPLE IV

Preparation of Prepolymer D

A prepolymer was prepared as in Example I, using 293.0 gm TPEPG10000 (TM) (Union Carbide Corp.), 23.92 gm IPDI and 0.16 gm Santonox R. TPEPG10000 is a 9000 MW triol prepared from 88% ethylene oxide and 12% propylene oxide polymerization monomers. The reactants were dissolved in 293.0 ml acetonitrile and synthesis was conducted as in Example I. After thirteen days the isocyanate content was 0.43 meq/gm (theoretical =0.31 meq/gm). The prepolymer was designated Prepolymer D.

EXAMPLE V

Preparation of Prepolymer E

A prepolymer was prepared as in Example I, using 572 gm BASF #46889 (a 7000 MW triol comprised of 80% ethylene oxide and 20% propylene oxide), 59.0 gm IPDI and 0.54 gm Santonox R. The reactants were dissolved in 572.0 ml acetonitrile and synthesis was performed as in Example I. After fourteen days the isocyanate content was 0.46 meq/gm (theoretical =0.39 meq/gm). This prepolymer was designated Prepolymer E.

EXAMPLE VI

Preparation of Prepolymer F

The prepolymer was prepared by mixing 79.0 gm Pluracol V10 (TM) (BASF) (a 22,000 MW diol comprised of 75% ethylene oxide and 25% propylene oxide), 0.24 gm trimethylolpropane and 2.94 gm IPDI. An antioxidant, Irganox 1076 (TM) (Ciba-Geigy Corp.) was added, to 0.05% of the total weight of the reactants (0.041 gm) and 150.0 ml acetonitrile was added to reduce viscosity. The synthesis was performed as in Example I. After eight days the isocyanate concentration was 0.18 meq/gm (theoretical estimated at approximately 0.24 meq/gm). This prepolymer was designated Prepolymer F.

EXAMPLE VII

Preparation of Prepolymer G

This prepolymer was prepared by heating to 60° C. a mixture of 0.031 moles homopolymer polyethylene glycol (~8000 MW) and 0.015 moles trimethylolpropane. The preheated mixture was added to 0.11 moles toluene diisocyanate (80% toluene-2,4-diisocyanate/20% toluene-2,6-diisocyanate isomer blend) over a period of about one hour, with stirring. After an additional hour of stirring, the isocyanate concentration reached a substantially constant value of 0.39 meq/gm (theoretical =0.40 meq/gm). This prepolymer was designated Prepolymer G and had the following idealized average composition:

OCN—T—(CH$_2$CH$_2$O)$_{181}$CH$_2$CH$_2$—T—NCO

OCN—T—(CH$_2$CH$_2$O)$_{181}$CH$_2$CH$_2$—T—NCO

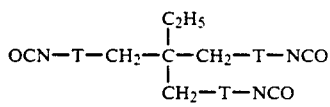

where T represents

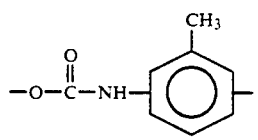

(the toluene diisocyanate urethane reaction moiety), and

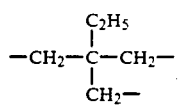

represents the trimethylolpropane reaction moiety. The calculated average composition of the Prepolymer G mixture comprised two moles of isocyanate-capped linear polymer of about 8350 MW for each mole of trifunctional isocyanate-capped crosslinker of about 656 MW. In effect, it is expected that when Prepolymer G is mixed with, and polymerized with, water or another aqueous liquid, it would react as though it has an effective molecular weight of about 17,000, or the sum of the weights of the three species depicted schematically above.

EXAMPLE VIII

Preparation of Prepolymer H

This prepolymer was prepared by heating to 60° C. a mixture of 0.04 moles homopolymer polyethylene glycol (~8000 MW) and 0.02 moles trimethylolpropane. The preheated mixture was added to 0.10 moles toluene diisocyanate (80% toluene-2,4-diisocyanate/20% toluene-2,6-diisocyanate isomer blend) over a period of about one hour, with stirring. The difference in concentration of ingredients yielded a different prepolymer than that obtained in Example VII. After an additional hour of stirring, the isocyanate concentration reached a substantially constant value of 0.20 meq/gm (theoretical =0.18 meq/gm). This prepolymer was designated Prepolymer H and had the following idealized average structure:

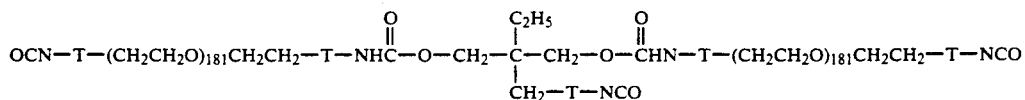

where T represents

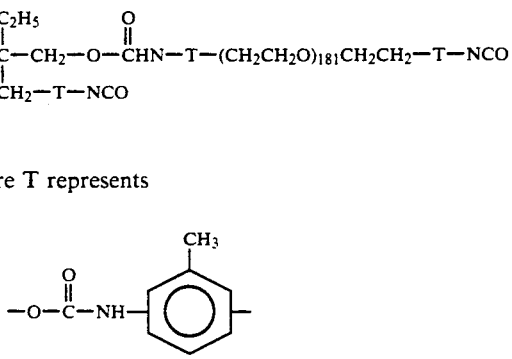

(the toluene diisocyanate urethane reaction moiety), and

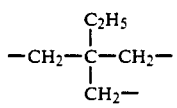

represents the trimethylolpropane reaction moiety. The calculated average molecular weight for Prepolymer H is about 17,000.

EXAMPLE IX

Preparation of Prepolymer J

A prepolymer was formed by repeating the preparation of Example I, except that the IPDI was replaced by an equivalent molar amount of toluene diisocyanate (80% toluene-2,4-diisocyanate/20% toluene-2,6-diisocyanate isomer blend). After heating for about seven hours, the isocyanate values reached 0.43 meq/gm (theoretical =0.40 meg/gm). This prepolymer, a liquid at room temperature, was designated Prepolymer J.

EXAMPLE X

Preparation of Prepolymer K

A prepolymer was prepared from a polyol designated WRG7000 (Union Carbide) after first removing water from it at 120° C. for 8 hours. The polyol (160 lbs.) was added to a 30 gallon stainless steel reactor with a steam jacket and a variable speed mixer. Isophorone diisocyanate (14.7 lbs.) was added and the mixture heated at 122° C. under nitrogen for 26.5 hours with stirring. The product had a viscosity of 72,000 cps and an isocyanate content of 0.46 meq/gm.

EXAMPLE XI

Preparation of Hydrated Polymer Coatings A-E

Hydrated polymer coatings were formed on particulate silica (particle size =10.0 μm; surface area =250 m2/gm), using Prepolymers A-E of the above Examples. The following procedure was used for each prepolymer.

On a sintered glass filter was placed 5.0 gm silica, and 50.0 ml of a 5.0% Prepolymer in acetonitrile solution was pulled through the silica bed with a vacuum. The solution was recovered and was passed repeatedly over the silica bed until the solvent had evaporated. Residual solvent was removed under vacuum for one hour at ambient temperatures. The coated particles were placed in a water bath at ambient temperatures for 17 hours to effect crosslinking and polymerization, then dried under vacuum at 50° C. for 17 hours.

The extent of coating achieved with each of the Hydrated Polymers A-E under these conditions was determined by thermal degradation analysis. For each polymer, 100.0 mg of coated particles were weighed before and after heating for five hours at 800° C. Table I shows the weight percent attributable to the hydrated polymer coating for each sample.

TABLE I

| Hydrated Polymer Coatings | |
|---|---|
| Prepolymer | Wt. % Loss on Heating |
| A | 10.0 |
| B | 13.7 |
| C | 8.5 |
| D | 6.5 |
| E | 12.5 |

EXAMPLE XII

Hydrated Polymer Coating Stability

The stability and durability of hydrated polymer coatings of this invention were compared with similarly obtained coatings of the precursor polyol. The coatings indicated in Table II were obtained by allowing solvent to evaporate from a suspension of silica, the coating substance and solvent. The silica used here had a 500 Angstrom pore diameter and a particle size of 20-45 microns. The suspension was formed by mixing 2.5 gm silica and 25 ml of 5% prepolymer or polyol in dichloromethane. The solvent was allowed to evaporate under ambient conditions. By using the evaporation procedure of this experiment, coating weights of about 25-30% were obtained, as compared with about 6-14% for the coating method described in Example X.

Coating durability was assessed by comparing the coating weight following preparation with the coating weight following washing as described here. All coating weights were measured by the thermal analysis method of Example X. The coated samples were washed with four 25.0 ml portions of 0.05M sodium phosphate (pH 8.0) then with four 25.0 ml portions of 0.1% trifluoroacetic acid in a 60/40 solution of isopropanol/water. The results, shown in Table II, demonstrate the substantially improved coating stability obtained by crosslinking on the substrate surface in the presence of water.

TABLE II

| Coating Stability | | |
|---|---|---|
| Coating | Washings | % Wt. Loss on Heating |
| Precursor polyol | None | 26.40 ± 0.28 |
| Precursor polyol | As described | 2.97 ± 0.18 |
| Prepolymer A | None | 30.53 ± 1.14 |
| Prepolymer A | As described | 28.80 ± 0.42 |

EXAMPLE XIII

Resistance to Protein Binding

To demonstrate the ability of the hydrated polymers of this invention to resist nonspecific protein binding or adsorption, a protein adsorptive surface was coated with prepolymer, which then was polymerized. Silica was chosen as the surface to be coated due to its ability to bind large amounts of protein. One gram of silica (particle size =10.0 $\mu$m, surface area =250.0 m$^2$/gm) was placed in a glass fritted filtering funnel. Fifty milliliters of a 5.0% solution of Prepolymer A in dry methylene chloride was passed over the bed repeatedly, under vacuum, until all solvent had evaporated. The coated silica was dried at 25° C. under vacuum for 16 hours, then placed in water overnight at 25° C. to allow polymerization to occur.

To determine the extent of protein binding, one gram of uncoated silica (control) and one gram of silica coated with the hydrated polymer each were mixed with 10.0 ml of 1.0 mg/ml hemoglobin in phosphate buffered saline ("PBS") (0.05M sodium phosphate, pH 7.0, 0.3M sodium chloride) for one hour at 25° C. The control and coated silicas were collected by filtration and were washed with PBS until 50.0 ml of the wash buffer were collected for each silica sample. Protein determinations were performed on each wash solution using the BioRad dye binding assay (BioRad Laboratories). The uncoated silica control was found to bind all of the 10.0 mg protein added. Protein binding to the silica coated with the hydrated polymer of this invention was below the limits of detection for this assay. Coating a surface normally adsorptive to protein with a polymer of this invention therefore reduced protein binding by >99%.

EXAMPLE XIV

Resistance to Protein Binding

Hydrated polymer coatings prepared from Prepolymers A-E were tested for resistance to protein binding. Silica (20-45 $\mu$m particle size; pore diameter =500A) was coated with each Prepolymer and polymerized as described in Example X. Protein binding to the coated silica was determined by incubating 0.2 gm silica with 50.0 mg hemoglobin in 10.0 ml phosphate buffered saline (0.01 M sodium phosphate, pH7) for one hour. The amount of hemoglobin bound to the polymer-coated silica then was measured using the BioRad dye binding reagent (BioRad Laboratories) in the presence of 80% sucrose in 0.05 M sodium borate (pH 7.0). After five minutes, the absorbance at 595 mm was measured and compared with an uncoated silica control. The protein rejection shown in Table III was expressed as a percent of the control.

TABLE III

| Rejection of Protein Binding | |
|---|---|
| Prepolymer Coating | Rejection of Protein Binding, % |
| A | 96.0 |
| B | 99.9 |
| C | 97.8 |
| D | 92.1 |
| E | 98.7 |

EXAMPLE XV

Hydrated Polymer Biocompatibility

Test samples of hydrated polymer were prepared by mixing ten parts (v/w) Dulbecco's Modified Eagle's Medium (DMEM) with one part Prepolymer A (see Example I). After mixing completely, several aliquots of the solution were transferred to 10 cm polystyrene petri dishes in such a manner that the entire surface was not covered but, rather, puddles or droplets were formed. The dishes were left at ambient temperatures for 30 minutes. After polymerization was complete, approximately 20% of the surface of each dish was covered with hydrated polymer. The dishes were sterilized by UV irradiation for 48 hours.

The cells used to test biocompatibility in this example were the LVC-PKI line (porcine kidney epithelial cell line obtained from American Type Culture Collection) which proliferate as a monolayer. At confluency, these cells cease proliferation and begin differentiation. The hallmark of differentiation by this cell line is the formation of domes, or raised groupings of cells, caused by accumulation of a fluid pocket under the cells as a result of vectorial transport of water and ions.

The petri dishes prepared above were inoculated with cells at near confluent densities in a suspension of culture medium (3:1 solution of DMEM:F12 cell culture medium) containing 1.0% fetal bovine serum and penicillin (100 IU/ml), streptomycin (100 gm/ml) and amphotericin B (250 ngm/ml). The dishes were incubated at 37° C. After 24 hours, a monolayer of cells had spread on the polystyrene surface. No cells has attached to the hydrated polymer but cells were visible on the polystyrene surface just adjacent to the polymer. After one week of culture at 37° C., the hydrated polymer surface remained free of cells. Cells growing on the polystyrene surface appeared identical to those in control cultures (with no hydrated polymer) and exhibited dome formation. It therefore is concluded that no toxic substances and/or inhibitors of cellular differentiation were present in the cultures containing the hydrated polymer.

EXAMPLE XVI

Polymer-Coated Test Tubes

Polystyrene test tubes, 12×75 mm, were coated with a 0.1% solution of Prepolymer A in methanol for one hour at room temperature. The solution was drained and the test tubes dried in a vacuum oven at room temperature for one hour. The polymer was crosslinked in place by covering with water for 17 hours at room temperature. The water was drained and the coated test tubes were air dried.

To determine the protein adsorptive capacity of these surfaces, five coated tubes and five untreated tubes were charged with 1.0 ml of IgG solutions in PBS (0.01 M sodium phosphate, 0.15 M sodium chloride, pH 7.4), the solutions containing 1, 2, 3, 4 or 5 μgm IgG. An additional set of four coated tubes were charged with 1.0 ml PBS without protein (that is, without IgG) to act as a control for possible interference by the polymer in the protein assay procedure. The tubes were placed in a Savant concentrator and the solutions evaporated to dryness overnight. This procedure generally results in significant protein loss due to protein sticking to the walls of the polystyrene tubes. After evaporation, 1.0 ml of distilled water was added to each tube and thoroughly agitated.

The solutions were transferred to untreated tubes and BioRad Protein Assay reagent (BioRad Laboratories) was added to the solutions. A standard curve was constructed using 1, 2, 3 ,4 and 5 μgm solutions of IgG as used initially. Deviation from values obtained with the standard curve would represent the amount of protein lost from each solution by adsorption onto the test tube. Compared with the control, the uncoated tubes gave an average recovery of approximately 72% while the coated tubes gave approximately 96%. Coating the polystyrene test tubes according to this invention resulted in dramatically increased protein recovery for each protein concentration.

EXAMPLE XVII

Polymer-coated Teflon (TM) Tubing

The inner surface of a piece of 2 mm i.d. Teflon (TM) polymer (E I. duPont de Nemours & Company) flexible tubing 6 inches in length was coated with Prepolymer A by supporting the ends of the tubing to form a U-shape, filling the tube with a 5% solution of the prepolymer in dry 2-propanol and allowing it to stand for one hour at room temperature. The solution was drained and the tube dried in a vacuum oven at room temperature for one hour. The tube was then immersed in an aqueous solution of 0.1 M Tris(hydroxymethyl aminomethane), pH 7.5, for 17 hours, again, at room temperature, to crosslink the polymer in place. The tube was then air dried for 24 hours.

EXAMPLE XVIII

Polymer-coated Silicone Tubing

Six-inch lengths of silicone tubing 1.5 mm in diameter were coated by contacting for two hours at room temperature with a 5% solution of Prepolymer A in methylene chloride. The solution was drained and the tubing air dried for 17 hours. The coated tubing was immersed in water for 17 hours to crosslink the polymer in place, and then air dried.

EXAMPLE XIX

Polymer-coated Arteriovenous Blood Tubing

An arteriovenous blood tubing set (Amicon Scientific Systems Division) made of Tygon (TM) vinyl polymer (U.S. Stoneware Co.), which is used with the Amicon Diafilter (TM) or Hemofilter (TM) hemofiltration sets in arteriovenous hemofiltration, was coated with Prepolymer A using a 5% polymer solution in 2-propanol as described in Example XVI. Three inch lengths of the 3.17 mm i.d. tubing were used.

EXAMPLE XX

Resistance to Protein Binding

An enzyme-linked immunosorbent assay (ELISA) was used to evaluate the effectiveness of the polymer coating in terms of its ability to prevent protein adsorption to the inner surface of the tubing. The antigen-antibody system used was bovine serum albumin (BSA) and polyclonal rabbit anti-BSA (Miles Scientific). Assays of this type are generally sensitive to nanogram quantities of antigen.

All procedures of this Example were conducted at room temperature. The coated tubing of Examples XVI, XVII and XVIII were tested according to the following procedures, as were uncoated tubing samples of the same three types.

Each piece of tubing was filled with a solution of BSA (10 mg/ml in PBS) and allowed to stand for two hours to allow time for protein binding to occur. The tubes were flushed thoroughly with PT buffer (PBS containing 0.5% Tween 20 (TM) (ICI United States, Inc.) to remove unbound protein. The tubes were then filled with the following solutions, in sequence, which were allowed to remain in the tube for the indicated times, in order to detect bound protein. Between each addition, the previous contents were flushed thoroughly from the tube with PT buffer.

1. Polyclonal rabbit anti-BSA, diluted 1:200 with PT buffer containing 5% chicken serum (this will be designated below as "PTCS"); one hour.
2. Biotinylated Protein A (Vector Laboratories), diluted 1:100 in PTCS; one hour.
3. Glucose Oxidase/Avidin (Vector Laboratories), diluted 1:200 with PT buffer; 15 minutes.
4. Enzyme substrate solution, which is comprised of the following:
   12.5 ml Phosphate-buffered 2,2'-azino-di-(3-ethyl-benzthiazoline sulfonic acid), ("ABTS", Sigma) prepared by dissolving the following in 250 ml water: 6.05 gm sodium phosphate, monobasic monohydrate; 1.65 gm sodium phosphate, dibasic heptahydrate, 40 mg ABTS, and 2.5 gm sodium cacodylate.
   1.5 ml Glucose—18% beta-D-glucose, prepared using alpha anomer and allowing to set overnight to effect mutarotation.
   0.5 ml Peroxidase—20 mg Type IV (Sigma) dissolved in 100 ml water.

The enzyme substrate solution was removed and replaced every 15 minutes and the absorbance at 410 nm was determined. A plot of absorbance versus time is proportional to the amount of BSA (protein) bound to the tube.

In all cases, substantial protein binding was seen with the uncoated tubes. By sharp contrast, protein binding was essentially eliminated for the coated tubing. Furthermore, when the tubes were placed in water for 17 hours, flushed with one liter of water and then re-tested as described above, identical results were obtained, demonstrating stability of the polymer coating.

EXAMPLE XXI

Polymer-coated Charcoal

The charcoal used for this work (BAC-MU, Kureha Chemical Industry Co., Ltd., Tokyo, Japan) was developed for use in hemoperfusion purification systems. It is spherical, has a surface area between 1000 and 1300 m²/gm, a particle size distribution between 0.42 and 1.0 mm, and a predominant pore size less than 60Å.

To 500 gm of this charcoal in a 3 l single neck round bottom flask was added one liter of a 10% (w/v) acetone solution of Prepolymer K. The flask was attached to a rotary evaporator and the solvent was removed over a 3 hour period under vacuum at a temperature of 30° C. The charcoal was further dried for 17 hours under vacuum at 40° C., after which it was cured for 24 hours by suspending the charcoal in 1.6 l water with shaking. The charcoal bed was then filtered and dried under vacuum for 17 hours prior to use.

EXAMPLE XXII

Resistance to Protein Binding

To demonstrate the ability of the hydrated polymers of this invention to resist nonspecific protein binding or adsorption, 0.5 gm charcoal coated as described in Example XX, and 0.5 gram of uncoated charcoal, each were mixed with 10.0 ml of 25 mg/ml bovine hemoglobin in phosphate buffered saline (0.01 M sodium phosphate, pH 7.4, 0.15 M sodium chloride) for seventeen hours at room temperature. The control and coated charcoal samples were centrifuged and the supernants diluted 200 times. Absorbances of the dilutes samples were measured using a Gilford Response Spectrophotometer at 410 nm..

TABLE IV

| | Hemoglobin Bonding |
|---|---|
| Sample | Hemoglobin bound (mg/gm) |
| Uncoated charcoal | 52.0 |
| Coated charcoal | 0.2 |

The uncoated charcoal was found to bind a significant amount of the protein added. Protein binding to charcoal coated with the hydrated polymer of the invention was essentially eliminated.

EXAMPLE XXIII

Hemolysis using Polymer-Coated Support

The effect of a hydrated polymer-coated purification device of the invention to resist non-specific protein binding or adsorption in red blood cell hemolysis was determined. Polymer-coated charcoal prepared as described in Example XX was chosen as the material to be tested.

Bovine whole blood was diluted with physiological saline (8.5 gm NaCl/l) to give a 2% suspension. Ten cc of the suspension was added to 0.5 gm of charcoal in triplicate in 50cc beakers and either kept in a static mode, or shaken at 200 rpm on an orbital platform shaker. After 1 hour, the cell suspension was centrifuged 2 minutes in a microcentrifuge and the absorbance of the supernatant, after an appropriate dilution with saline, was measured at 410 nm. The average values obtained are reported below.

| | Absorbance at 410 nm ± s.d. | |
|---|---|---|
| Sample | Static | Shaken |
| None | 0.181 ± 0.011 | 0.781 ± 0.010 |
| Bare charcoal | 5.849 ± 0.349 | 13.540 ± 0.200 |
| Polymer-coated charcoal | 0.331 ± 0.027 | 3.049 ± 0.331 |

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

We claim:

1. A biocompatible, protein non-adsorptive medical or laboratory device having a polymer coating on at least one surface thereof in which the polymer of said polymer coating is a hydrophilic, biocompatible hydrated polyurea-urethane polymer gel derived from prepolymer units at least 75% of which are oxyethylene-based diols or polyols having molecular weights of about 7000 to about 30,000, said diols or polyols having essentially all of the hydroxyl groups capped with polyisocyanate, said hydrated polymer gel characterized by transparency and by a surface having improved resistance to nonspecific protein adsorption, an formed by reacting said prepolymer units with water.

2. The polymer-coated device of claim 1 in which at least 90% of said prepolymer units are polyisocyanate-capped oxyethylene-based diols or polyols.

3. The polymer-coated device of claim 1 in which all of said prepolymer units are polyisocyanate-capped oxyethylene-based diols or polyols.

4. The polymer-coated device of claim 1 in which the molecular weight of said diols or polyols prior to capping with polyisocyanate is at least 10,000.

5. The polymer-coated device of claim 1 in which said diols or polyols are capped with an aliphatic or cycloaliphatic polyisocyanate.

6. The polymer-coated device of claim 5 in which said polyisocyanate is isophorone diisocyanate.

7. The polymer-coated device of claim 1 in which the polymer comprises an antioxidation agent.

8. The polymer-coated device of claim 1 in which said device comprises rubber, silicone, polyurethane polymer, Teflon (TM) polymer, polystyrene, woven or non-woven cloth or cloth-like material, silica or glass, charcoal, polyvinylchloride, poly-methylpentene, metal, wood or Tygon (TM) vinyl polymer.

9. The polymer-coated device of claim 1 which is a filter, an artificial organ or portion thereof, a extracorpeal therapeutic device, a cell culture or bioreactor system, device or portion thereof, or a protein isolation, preparation or purification device or system or portion thereof.

10. The polymer-coated device of claim 1 which is prepared by depositing a prepolymer-organic solvent solution on the uncoated device, removing excess organic solvent and then reacting the prepolymer with water to promote crosslinking on the substrate surface.

11. The polymer-coated device of claim 10 in which said organic solvent is selected from acetonitrile, dimethyl formamide, dimethyl sulfoxide, tetrahydrofuran, dioxane, acetone, methyl ethyl ketone, methanol, ethanol, 2-propanol, methylene chloride, dichloromethane, or mixtures thereof.

12. The polymer-coated device of claim 10 which comprises a monomolecular or substantially monomolecular layer on a coatable substrate.

13. The polymer-coated device of claim 1 which is prepared by depositing a prepolymer-organic solvent solution on the uncoated device, drying and then reacting the prepolymer with water to promote crosslinking on the substrate surface.

14. The polymer-coated device of claim 1 which is prepared by depositing a prepolymer-organic solvent solution on the uncoated device and reacting the prepolymer with water to promote crosslinking on the substrate surface.

15. A method for improving medical or laboratory devices to increase biocompatibility and resistance to protein binding, comprising
 a) preparing a prepolymer-organic solvent solution, at least 75% of the prepolymer units of said prepolymer consisting of oxyethylene-based diols or polyols having molecular weights of about 7000 to about 30,000, said diols or polyols having essentially all of the hydroxyl groups capped with polyisocyanate,
 b) depositing said solution on a medical or laboratory device or portion thereof,
 c) forming a coating on said device, and
 d) reacting said coated device with water to promote crosslinking.

16. The method of claim 15 in which the coating of step (c) is formed by drying.

17. The method of claim 15 in which said solution is deposited on said device by immersing said device in the solution.

18. The method of claim 15 in which the coating of step (c) is formed by allowing prepolymer to become deposited on, adsorbed to or impregnated in the surface of said device, and removing excess solution.

19. The method of claim 15 in which at least 90% of the prepolymer units are polyisocyanate-capped oxyethylene-based diols or polyols.

20. The method of claim 19 in which all of said prepolymer units are polyisocyanate-capped oxyethylene-based diols or polyols.

21. The method of claim 15 in which the prepolymer concentration of said solution is between about 0.01% and about 10.0% by weight.

22. The polymer-coated device of claim 9 in which the protein isolation, preparation or purification device is a membrane or particulate media.

23. The polymer-coated device of claim 22 in which said particulate media is a silica or charcoal particle.

24. A hemoperfusion system comprising the polymer-coated device of claim 1.

25. A hemoperfusion system of claim 24 in which the polymer-coated device is a filter or tubing.

26. A hemoperfusion system comprising the polymer-coated device of claim 23.

27. A diagnostic assay system comprising the polymer-coated device of claim 1.

* * * * *

UNITED STATES PATENT AND TRADEMARK OFFICE
CERTIFICATE OF CORRECTION

PATENT NO. : 5,169,720
DATED : December 8, 1992
INVENTOR(S) : James Anthony Braatz et al.

It is certified that error appears in the above-identified patent and that said Letters Patent is hereby corrected as shown below:

In claim 1, column 23 at line 10, delete "an" and insert --and--.

Signed and Sealed this

Second Day of November, 1993

Attest:

BRUCE LEHMAN

Attesting Officer    Commissioner of Patents and Trademarks